United States Patent
Kawai

(10) Patent No.: US 10,502,685 B2
(45) Date of Patent: Dec. 10, 2019

(54) METHOD FOR URINE SAMPLE ANALYSIS, REAGENT FOR URINE SAMPLE ANALYSIS, AND REAGENT KIT FOR URINE SAMPLE ANALYSIS

(71) Applicant: SYSMEX CORPORATION, Kobe-shi, Hyogo (JP)

(72) Inventor: Akinori Kawai, Kobe (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 16 days.

(21) Appl. No.: 15/121,250

(22) PCT Filed: Feb. 27, 2015

(86) PCT No.: PCT/JP2015/055897
§ 371 (c)(1),
(2) Date: Aug. 24, 2016

(87) PCT Pub. No.: WO2015/129869
PCT Pub. Date: Sep. 3, 2015

(65) Prior Publication Data
US 2016/0363535 A1    Dec. 15, 2016

(30) Foreign Application Priority Data
Feb. 28, 2014   (JP) ................. 2014-039281

(51) Int. Cl.
| | | |
|---|---|---|
| *G01N 21/64* | (2006.01) | |
| *G01N 33/493* | (2006.01) | |
| *G01N 21/49* | (2006.01) | |
| *G01N 33/52* | (2006.01) | |
| *G01N 33/80* | (2006.01) | |
| *G01N 15/14* | (2006.01) | |
| *G01N 15/00* | (2006.01) | |

(52) U.S. Cl.
CPC ..... *G01N 21/6428* (2013.01); *G01N 15/1434* (2013.01); *G01N 21/49* (2013.01); *G01N 21/6458* (2013.01); *G01N 33/493* (2013.01); *G01N 33/52* (2013.01); *G01N 33/80* (2013.01); *G01N 2015/0065* (2013.01); *G01N 2021/6439* (2013.01); *G01N 2201/06113* (2013.01)

(58) Field of Classification Search
CPC ........... G01N 21/6428; G01N 15/1434; G01N 21/6458; G01N 21/49; G01N 33/80; G01N 2021/6439; G01N 2201/06113; G01N 2015/0065
See application file for complete search history.

(56) References Cited

U.S. PATENT DOCUMENTS

| | | |
|---|---|---|
| 5,693,484 A | 12/1997 | Nakamoto et al. |
| 5,891,733 A | 4/1999 | Inoue |
| 2002/0076743 A1* | 6/2002 | Sakai .................. C12Q 1/04 435/34 |
| 2003/0224445 A1 | 12/2003 | Hotta et al. |
| 2006/0073601 A1 | 4/2006 | Kawashima et al. |
| 2009/0050821 A1* | 2/2009 | Tanaka ............... G01N 15/1459 250/458.1 |

FOREIGN PATENT DOCUMENTS

| | | |
|---|---|---|
| EP | 0 708 334 A2 | 4/1996 |
| EP | 2 963 418 A1 | 1/2016 |
| JP | 4-337459 A | 11/1992 |
| JP | 8-240520 A | 9/1996 |
| JP | 9-329596 A | 12/1997 |
| JP | 11-23446 A | 1/1999 |
| JP | 2002-90365 A | 3/2002 |
| JP | 2006105625 A | 4/2006 |
| JP | 2015/055897 A | 5/2015 |

OTHER PUBLICATIONS

International Search Report of PCT/JP2015/055897 dated May 26, 2015.
Brazilian Office Action dated Oct. 8, 2019 in a counterpart Brazilian patent application No. BR112016019579-5.

* cited by examiner

*Primary Examiner* — Sean C. Barron
(74) *Attorney, Agent, or Firm* — Sughrue Mion, PLLC

(57) ABSTRACT

The present invention relates to a method for analyzing urine sample, a reagent for analysis of urine sample and a reagent kit for analysis of urine sample, which are for detecting at least casts and erythrocytes as urinary particles.

14 Claims, 1 Drawing Sheet

METHOD FOR URINE SAMPLE ANALYSIS, REAGENT FOR URINE SAMPLE ANALYSIS, AND REAGENT KIT FOR URINE SAMPLE ANALYSIS

TECHNICAL FIELD

The present invention relates to a method for analyzing urine sample, a reagent for analysis of urine sample and a reagent kit for analysis of urine sample, which are for detecting at least casts and erythrocytes as urinary particles.

BACKGROUND ART

In diseases such as infectious diseases, inflammatory lesions, degenerative lesions, calculus diseases, tumors and the like in nephric and urinary systems, a variety of particles appear in the urine depending on the individual diseases. The particles may include erythrocytes, casts, leukocytes, epithelial cells, yeast like fungi, spermatozoa and the like. Analysis of these particles in the urine is important for estimating the disease and the abnormal site in nephric and urinary systems. For example, erythrocytes are useful urinary particles for determining the presence or absence of bleeding in the route from the glomerulus of the kidney to the urethra.

A cast is a solid particle having a coagulation precipitate composed of Tamm-Horsfall mucoprotein and urinary plasma protein (principally albumin) as a basic component. The cast is formed principally in the distal renal tubule and the collecting tubule. While the cast composed exclusively of the basic component is called a hyaline cast, various components such as cells may be enclosed in the hyaline cast depending on the condition of the kidney or the renal tubule, with the result that a further degenerated cast could be formed. Therefore, the casts are useful urinary particles for grasping the disease condition and the degree of the disorder of the kidney and the renal tubule.

In analysis of the urinary particles such as casts and erythrocytes, a visual inspection is widely conducted by observing the precipitate (particles) obtained by centrifugal separation of the urine under a microscope. In recent years, an automated analysis method using a flow cytometer has been developed. For example, Patent Documents 1 to 4 disclose a method for analyzing urinary particles with a flow cytometer by measuring a urine sample treated with a diluting reagent, and a staining reagent containing a cyanine-based dye, 3,3'-dihexyl-2,2'-oxacarbocyanine iodide (DiOC6(3)) for staining urinary particles.

Meanwhile, the urine also contains the particles which extremely resemble the casts in shape, such as mucus threads and aggregates of bacteria or salts. Since the number of casts in a urine sample is the clinically important information, it is important for the detection of the casts to discriminate the casts from the particles which resemble the casts, such as mucus threads.

CITATION LIST

Patent Documents

Patent Document 1: Japanese Unexamined Patent Publication No. HEI 11(1999)-23446
Patent Document 2: Japanese Unexamined Patent Publication No. HEI 9(1997)-329596
Patent Document 3: Japanese Unexamined Patent Publication No. HEI 8(1996)-240520
Patent Document 4: Japanese Unexamined Patent Publication No. HEI 8(1996)-170960

SUMMARY OF THE INVENTION

Problems to be Solved by the Invention

An object of the present invention is to provide a method for analyzing urine sample that allows accurate detection of erythrocytes without causing hemolysis and accurate detection of casts discriminably from impurities such as mucus threads compared to the prior art. Further, an object of the present invention is to provide a reagent and a reagent kit for analysis of urine sample that are suitably used for the method.

Solution to the Problems

As a result of diligent efforts, the present inventors have found that by using a specific cyanine-based fluorescent dye as a dye for staining urine particles, erythrocytes can be detected without substantially damaging them, and casts can be detected discriminably from mucus threads, thereby achieving the present invention.

Therefore, the present invention provides a method for analyzing a urine sample, comprising the steps of preparing a measurement sample by mixing the urine sample and a first reagent containing at least one fluorescent dye selected from 3,3'-diethyloxacarbocyanine iodide (DiOC2(3)), 3,3-dipropyloxacarbocyanine iodide (DiOC3(3)), 3,3'-dibutyloxacyanine iodide (DiOC4(3)) and 3,3-dipentyloxacarbocyanine iodide (DiOC5(3)), and detecting at least casts and erythrocytes as urinary particles contained in the measurement sample obtained in the preparation step.

The present invention also provides a reagent for analysis of urine sample for detecting at least casts and erythrocytes as urinary particles, containing at least one fluorescent dye selected from DiOC2(3), DiOC3(3), DiOC4(3) and DiOC5(3).

Further, the present invention provides a reagent kit for analysis of urine sample for detecting at least casts and erythrocytes as urinary particles, comprising a first reagent containing at least one fluorescent dye selected from DiOC2(3), DiOC3(3), DiOC4(3) and DiOC5(3), and a second reagent containing a surfactant as a dispersant.

Effects of the Invention

The present invention allows detection of erythrocytes without substantially damaging them and accurate detection of casts and erythrocytes.

EMBODIMENTS OF THE INVENTION

Figure 1:
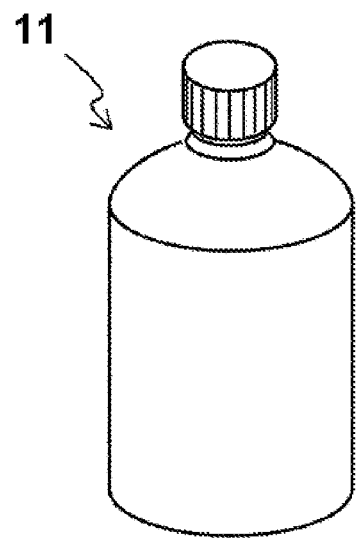
FIG. 1 shows one example of a reagent for analysis of urine sample.

[Method for Analyzing Urine Sample]
A method for analyzing a urine sample (hereinafter, also simply referred to as "method") of the present embodiment is intended to analyze erythrocytes, casts, crystal components and mucus threads among urinary particles, and is particularly preferred for analyzing casts and erythrocytes.

Various kinds of casts are known, for example, hyaline casts that are composed exclusively of the above-described basic component, epithelial casts in which renal tubular epithelial cells are enclosed, red blood cell casts in which erythrocytes are enclosed, white blood cell casts in which leukocytes are enclosed, fatty casts in which fatty granules are enclosed, granular casts in which granular components (principally the degenerated epithelial cells) are enclosed, and waxy casts in which the entire or part of the casts are uniform and degenerated as a wax. In the present embodiment, the kind of casts is not particularly limited.

In the present embodiment, the kind of erythrocytes is not particularly limited, and may include any of normal erythrocytes and abnormal erythrocytes.

In the method of the present embodiment, first, a step of preparing a measurement sample by mixing a urine sample and a first reagent containing at least one fluorescent dye selected from 3,3'-diethyloxacarbocyanine iodide (DiOC2(3)), 3,3-dipropyloxacarbocyanine iodide (DiOC3(3)), 3,3'-dibutyloxacyanine iodide (DiOC4(3)) and 3,3-dipentyloxacarbocyanine iodide (DiOC5(3)) is conducted.

In the present embodiment, the urine sample is not particularly limited as far as it is a liquid sample containing the urinary particles, and is preferably the urine collected from a subject. In the case of using the urine collected from the subject as a sample, it is desired to use the urine sample for the method of the present embodiment within 24 hours, particularly within 3 to 12 hours after collection because the urinary particles may be deteriorated with time.

The first reagent used in the method of the present embodiment is a reagent for staining urinary particles containing at least casts and erythrocytes. The fluorescent dyes DiOC2(3), DiOC3(3), DiOC4(3) and DiOC5(3) that can be used in the first reagent are also referred to as NK-85, NK-2605, NK-5587 and NK-2453, respectively, and are available from HAYASHIBARA CO., LTD. In conventional analysis methods, a staining reagent containing 3,3'-dihexyl-2,2'-oxacarbocyanine iodide (DiOC6(3)) which is a cyanine-based dye for staining urinary particles is used. The present inventors have found that the form of erythrocytes in the sample can be kept more favorably and the erythrocytes can be detected more accurately by treating the urine sample with a staining reagent containing at least one fluorescent dye selected from DiOC2(3), DiOC3(3), DiOC4(3) and DiOC5(3) rather than treating the urine sample with a staining reagent containing DiOC6(3). In the method of the present embodiment, membrane components of erythrocytes and casts are favorably stained by these dyes, whereas mucus threads are little stained. The structural formula of these dyes are shown below.

[Chemical formula 1]

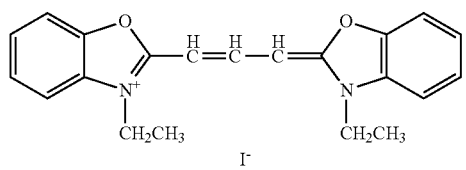

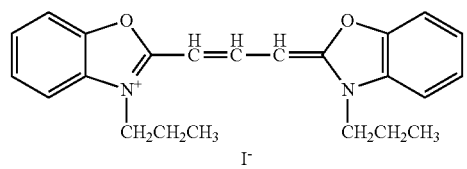

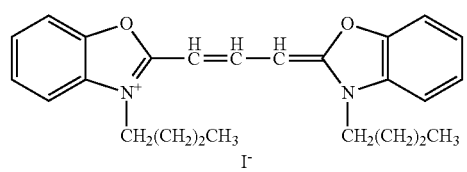

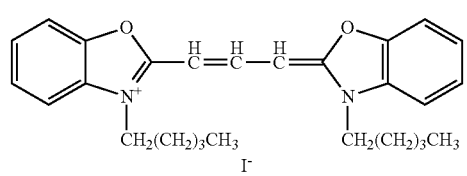

The first reagent may contain one fluorescent dye or two or more fluorescent dyes. The concentration of the fluorescent dye in the first reagent is desirably set so that the fluorescent dye is contained in such a final concentration capable of appropriately staining at least casts and erythrocytes in the prepared measurement sample. The final concentration in the measurement sample may be appropriately set depending on the kind of the fluorescent dye. For example, when DiOC3(3) is used as the fluorescent dye, the final concentration in the measurement sample is more than or equal to 0.1 µg/mL and less than or equal to 200 µg/mL, preferably more than or equal to 1 µg/mL and less than or equal to 20 µg/mL.

The first reagent can be obtained by dissolving the aforementioned fluorescent dye in an appropriate solvent. The solvent is not particularly limited as far as it is an aqueous solvent capable of dissolving the fluorescent dye and examples thereof include water, a water-soluble organic solvent and a mixture thereof. Among these, a water-soluble organic solvent is particularly preferable. Examples of the water-soluble organic solvent include lower alcohols having 1 to 3 carbon atoms, ethylene glycol, dimethylsulfoxide (DMSO) and the like.

In the present embodiment, a diluting reagent for diluting the urine sample may be further mixed as needed in the preparation step. As such a diluting reagent, water or a buffer solution is preferable. The buffer solution is not particularly limited as far as it is an aqueous solution of a buffer having a buffering action at the pH range of higher than or equal to 5 and lower than or equal to 9, preferably at the range of higher than or equal to 6.5 and lower than or equal to 8.6, and more preferably at the range of higher than or equal to 7.0 and lower than or equal to 7.8. Examples of the buffer include Good's buffers such as Tris, MES, Bis-Tris, ADA, PIPES, ACES, MOPS, MOPSO, BES, TES, HEPES, DIPSO, TAPSO, POPSO, HEPPSO, EPPS, Tricine, Bicine, TAPS and the like.

In the present embodiment, it is preferred to further mix a second reagent containing a surfactant as a dispersant in the preparation step. By further mixing such a second reagent, the aggregates of the impurities such as bacteria or salts that inhibit accurate detection of casts can be dispersed and removed.

The second reagent can be obtained by dissolving a surfactant in an appropriate solvent. The solvent is not particularly limited as far as it can dissolve the surfactant and may include, for example, water, a water-soluble organic solvent and a mixture thereof. Examples of the water-soluble organic solvent include lower alcohols having 1 to 3 carbon atoms, ethylene glycol and DMSO. In the present embodiment, water is particularly preferred. The second reagent may be prepared by dissolving a surfactant in the aforementioned diluting reagent.

The kind of the surfactant used in the second reagent is not particularly limited, and can be appropriately selected from cationic surfactants, nonionic surfactants, anionic surfactants and amphoteric surfactants. The first reagent may contain one surfactant or two or more surfactants. When two or more surfactants are contained, the combination thereof may be optionally selected.

In the present embodiment, as the cationic surfactant, at least one selected from quaternary ammonium salt type surfactants and pyridinium salt type surfactants may be used. The quaternary ammonium salt type surfactant may include, for example, the surfactants having 9 to 30 carbon atoms in total represented by the following formula (I).

[Chemical formula 2]

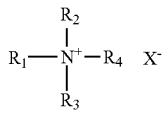

(I)

In the above formula (I), $R_1$ is an alkyl or alkenyl group having 6 to 18 carbon atoms; $R_2$ and $R_3$ are the same or different from each other and are respectively an alkyl or alkenyl group having 1 to 4 carbon atoms; $R_4$ is an alkyl or alkenyl group having 1 to 4 carbon atoms, or a benzyl group; and $X^-$ is a halogen ion In the above formula (I), $R_1$ is preferably an alkyl group or an alkenyl group having 6, 8, 10, 12 or 14 carbon atoms and is particularly preferably a linear alkyl group. More specifically, $R_1$ may include an octyl group, a decyl group and a dodecyl group. $R_2$ and $R_3$ are preferably a methyl group, an ethyl group and a propyl group. $R_4$ is preferably a methyl group, an ethyl group and a propyl group.

The pyridinium salt type surfactant may include, for example, the surfactants represented by the following formula (II).

[Chemical formula 3]

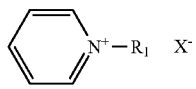

(II)

In the above formula (II), $R_1$ is an alkyl or alkenyl group having 6 to 18 carbon atoms; and $X^-$ is a halogen ion.

In the above formula (II), $R_1$ is preferably an alkyl or alkenyl group having 6, 8, 10, 12 or 14 carbon atom and is particularly preferably a linear alkyl group. More specifically, $R_1$ include an octyl group, a decyl group and a dodecyl group.

Specific examples of the cationic surfactant include dodecyltrimethylammonium bromide, decyltrimethylammonium bromide, dodecyltrimethylammonium chloride, octyltrimethylammonium bromide, octyltrimethylammonium chloride, myristyltrimethylammonium bromide, myristyltrimethylammonium chloride, dodecylpyridinium chloride and the like. Among these, dodecyltrimethylammonium bromide (DTAB) is particularly preferred.

In the present embodiment, as the nonionic surfactant, the polyoxyethylene-based nonionic surfactants represented by the following formula (III) are preferably used.

$$R_1-R_2-(CH_2CH_2O)_n-H \quad (III)$$

In the above formula (III), $R_1$ is an alkyl, alkenyl or alkynyl group having 8 to 25 carbon atoms; $R_2$ is —O—, —COO— or

[Chemical formula 4]

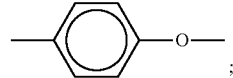

;

and n represents an integer of 10 to 50.

Specific examples of the nonionic surfactant include polyoxyethylene alkyl ether, polyoxyethylene sterol, polyoxyethylene castor oil, polyoxyethylene sorbit fatty acid ester, polyoxyethylene alkyl amine, polyoxyethylene polyoxypropylene alkyl ether and the like.

In the present embodiment, as the anionic surfactant, at least one kind selected from the carboxylate type surfactants, the sulfonate type surfactants and the sulfuric acid ester salt type surfactants may be used. The carboxylate type surfactant includes, for example, the surfactants represented by the following formula (IV).

$$R_1-COO^-Y^+ \quad (IV)$$

In the above formula (IV), $R_1$ is an alkyl, alkenyl or alkynyl group having 8 to 25 carbon atoms; and $Y^+$ is an alkali metal ion.

In the above formula (IV), $R_1$ is preferably a linear alkyl group having 12 to 18 carbon atoms. The carboxylate type surfactants are known as soap in the art and examples thereof include sodium laurate, sodium stearate, sodium oleate and the like.

The sulfonate type surfactant may include, for example, the surfactants represented by the following formula (V).

[Chemical formula 5]

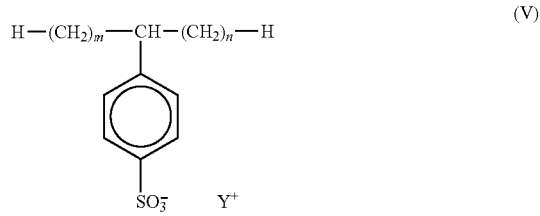

(V)

In the above formula (V), m and n are an integer of 0 or more, the sum of m and n is 8 to 25; and $Y^+$ is an alkali metal ion.

Preferably, the sum of m and n in the formula (V) is 9 to 18. The sulfonate type surfactants represented by the above formula (V) are known as alkyl benzene sulfonates in the art and examples thereof include sodium linear decylbenzene sulfate, sodium linear undecylbenzene sulfate, sodium linear dodecylbenzene sulfate, sodium linear tridecylbenzene sulfate, sodium linear tetradecylbenzene sulfate and the like.

Also, as the sulfonate type surfactant, a mixture of surfactants respectively represented by the following formulas (VI) and (VII) may be used.

$$CH_3(CH_2)_j—CH=CH—(CH_2)_k—SO_3^-Y^+ \qquad (VI)$$

In the above formula (VI), j and k are an integer of 0 or more, the sum of j and k is an integer of 10 to 25; and $Y^+$ is an alkali metal ion.

$$CH_3(CH_2)_m—CH(—OH)—(CH_2)_n—SO_3^-Y^+ \qquad (VII)$$

In the above formula (VII), m and n are an integer of 0 or more, the sum of m and n is an integer of 10 to 25; and $Y^+$ is an alkali metal ion.

Preferably, the sum of j and k in the above formula (VI) is an integer of 11 to 15, and the sum of m and n in the above formula (VII) is an integer of 12 to 16. The surfactants respectively represented by the above formulas (VI) and (VII) are also known as α-olefin sulfonates in the art and examples thereof include sodium 1-tetradecene sulfonate, sodium hexadecene sulfonate, sodium 3-hydroxyhexadecyl-1-sulfonate, sodium octadecene-1-sulfonate, sodium 3-hydroxy-1-octadecane sulfonate and the like.

The sulfuric acid ester salt type surfactant may include, for example, the surfactants represented by the following formula (VIII).

$$R_1—O—SO_3^-Y^+ \qquad (VIII)$$

In the above formula (VIII), $R_1$ represents an alkyl, alkenyl or alkynyl group having 10 to 25 carbon atoms; and Y± represents an alkali metal ion.

In the above formula (VIII), $R_1$ is preferably a linear alkyl group having 10 to 18 carbon atoms, and is particularly preferably a linear alkyl group having 12 carbon atoms. The sulfuric acid ester salt type surfactants represented by the above formula (VIII) are known as higher alcohol sulfate salt in the art and examples thereof include sodium decyl sulfate, sodium undecyl sulfate, sodium dodecyl sulfate, sodium tridecyl sulfate, sodium tetradecyl sulfate and the like.

Also, as the sulfuric acid ester salt type surfactant, the surfactants represented by the following formula (IX) may be used.

$$R_1—O—(CH_2CH_2O)_n—SO_3^-Y^+ \qquad (IX)$$

In the above formula (IX), $R_1$ is an alkyl, alkenyl or alkynyl group having 10 to 25 carbon atoms; n is an integer of 1 to 8; and $Y^+$ is an alkali metal ion or an ammonium ion.

In the above formula (IX), $R_1$ is preferably a linear alkyl having 12 to 18 carbon atoms, and is particularly preferably a linear alkyl group having 12 carbon atoms. The sulfuric acid ester salt type surfactants represented by the above formula (IX) are known as polyoxyethylene alkyl sulfuric acid ester salt in the art and examples thereof include sodium dodecyl ether sulfuric acid ester and the like.

As the sulfuric acid ester salt type surfactant, a surfactant represented by the following formula (X) may be used.

$$R_1—CH(—SO_3^-)—COOCH_3Y^+ \qquad (X)$$

In the above formula (X), $R_1$ is an alkyl, alkenyl or alkynyl group having 8 to 25 carbon atoms; and $Y^+$ is an alkali metal ion.

In the above formula (X), $R_1$ is preferably a linear alkyl group having 10 to 18 carbon atoms, and is particularly preferably a linear alkyl group having 12 carbon atoms. The sulfuric acid ester salt type surfactants represented by the above formula (X) are known as α-sulfo fatty acid esters in the art and examples thereof include 2-sulfotetradecanoic acid-1-methylester sodium salt, 2-sulfohexadecanoic acid-1-methylester sodium salt and the like.

In the present embodiment, as the amphoteric surfactant, at least one kind selected from amino acid type amphoteric surfactants and betaine type amphoteric surfactants may be used. The amino acid type amphoteric surfactant may include, for example, the surfactants represented by the following formula (XI).

$$R_1—N^+H_2—CH_2CH_2COO^- \qquad (XI)$$

In the above formula (XI), $R_1$ is an alkyl, alkenyl or alkynyl group having 8 to 25 carbon atoms.

In the above formula (XI), $R_1$ is preferably a linear alkyl group having 12 to 18 carbon atoms. The above amino acid type amphoteric surfactant may include, for example, 3-(dodecylamino)propanoic acid, 3-(tetradeca-1-ylamino)propanoic acid and the like.

The betaine type amphoteric surfactant include, for example, the surfactants represented by the following formula (XII).

[Chemical formula 6]

(XII)

In the above formula (XII), $R_1$ is an alkyl or alkenyl group having 6 to 18 carbon atoms; $R_2$ is an alkyl or alkenyl group having 1 to 4 carbon atoms; $R_3$ is an alkyl or alkenyl group having 1 to 4 carbon atoms, or a benzyl group; and n is 1 or 2.

The betaine type amphoteric surfactant may include, for example, dodecyldimethylaminoacetic acid betaine, stearyldimethylaminoacetic acid betaine and the like.

The concentration of the surfactant in the second reagent is desirably set so that the surfactant is contained in such a final concentration that erythrocytes are not hemolyzed and aggregates of impurities can be dispersed in the measurement sample prepared in the manner as described above. The final concentration of the surfactant in the measurement sample can be appropriately set, and is preferably more than or equal to 3 ppm and less than or equal to 30 ppm.

In the present embodiment, in order to prevent hemolysis of erythrocytes due to change in pH, pH of the second reagent can be adjusted in a range of higher than or equal to 5 and lower than or equal to 9, preferably in a range of higher than or equal to 6.5 and lower than or equal to 8.6, and more preferably in a range of higher than or equal to 7.0 and lower than or equal to 7.8. Therefore, in order to keep pH constant, the second reagent may contain a buffer. Such a buffer may be the same as that used in the above diluting reagent.

Some urine samples contain amorphous salts such as ammonium phosphate, magnesium phosphate and calcium carbonate. In the present embodiment, the second reagent may contain a chelating agent for reducing the influence of these amorphous salts. The chelating agent is not particularly limited as far as it is a chelating agent capable of removing amorphous salts, and can be appropriately selected from calcium removing agents and magnesium removing agents that are known in the art. Specific examples include ethylenediaminetetraacetate (EDTA salt), CyDTA, DHEG, DPTA-OH, EDDA, EDDP, GEDTA, HDTA, HIDA, Methyl-EDTA, NTA, NTP, NTPO, EDDPO and the like, and among these, EDTA salt is particularly preferable.

The concentration of the chelating agent in the second reagent is desirably set so that the chelating agent is contained in such a final concentration that can reduce the influence of the amorphous salts in the measurement sample prepared in the manner as described above. The final concentration in the measurement sample may be appropriately set depending on the kind of the chelating agent. For example, when EDTA 2 potassium (EDTA-2K) is used as the chelating agent, the final concentration in the measurement sample is more than or equal to 0.1 mM and less than or equal to 500 mM, preferably more than or equal to 1 mM and less than or equal to 100 mM.

It is known that in the case where yeast like fungi and erythrocytes are present in the urine, fractionation between the yeast like fungi and the erythrocytes is sometimes not good in the analysis by a flow cytometer. Therefore, the second reagent may contain a substance that damages cell membranes of yeast like fungi. Examples of such a substance include 2-phenoxy ethanol, benzyl alcohol, phenethyl alcohol, 1-phenoxy-2-propanol, phenol, phenyl acetate, benzothiazole and the like, and among these, 2-phenoxy ethanol is particularly preferable. By using the second reagent containing such a substance, the stainability of the yeast like fungi changes, and fractionation between the erythrocytes and the yeast like fungi is improved.

The osmotic pressure of urine is known to distribute in a wide range of 50 to 1300 mOsm/kg. When the osmotic pressure is too low or too high in the measurement sample, there is a fear that erythrocytes are damaged. An appropriate osmotic pressure in the measurement sample is more than or equal to 100 mOsm/kg and less than or equal to 600 mOsm/kg, preferably more than or equal to 150 mOsm/kg and less than or equal to 500 mOsm/kg. When the osmotic pressure of the urine is too high, the osmotic pressure can be appropriately adjusted by diluting the urine with a diluting reagent or the second reagent. On the other hand, when the osmotic pressure of the urine is too low, the second reagent may contain an osmotic pressure compensating agent. The osmotic pressure compensating agent may include inorganic salts, organic salts, saccharides and the like. Examples of the inorganic salts include sodium chloride, sodium bromide and the like. Examples of the organic salts include sodium propionate, potassium propionate, ammonium propionate oxalate and the like. Examples of the saccharides include sorbitol, glucose, mannitol and the like.

In the present embodiment, the urine sample, the first reagent, and the second reagent may be mixed in any order without limitation, and these may be mixed at the same time. Preferably, the urine sample and the second reagent are mixed previously, and then the first reagent is further mixed therein. Alternatively, the first reagent and the second reagent may be mixed previously, and then the urine sample may be further mixed therein.

In the present embodiment, the mixing ratio of the urine sample, the first reagent, and the second reagent is not particularly limited, and may be appropriately determined depending on the component concentrations contained in the respective reagents. For example, the mixing ratio between the urine sample and the first reagent can be determined within the range of 1:0.01 to 10 by volume ratio. The mixing ratio between the urine sample and the second reagent can be determined within the range of 1:0.5 to 1 by volume ratio. The amount of the urine sample can be appropriately determined depending on the first reagent and the second reagent. The amount of the urine sample is preferably less than or equal to 1000 μL so that the measurement time is not too long. A sufficient amount of the urine sample used for the measurement is about 10 to 1000 μL.

The temperature condition in the preparation step is 10 to 60° C., preferably 35 to 45° C. Each reagent may be previously heated to the above temperature. After mixing the urine sample, the first reagent and/or the second reagent, the mixture may be incubated for 1 second to 5 minutes, preferably 5 to 60 seconds.

In the method of the present embodiment, the step of detecting at least casts and erythrocytes as urinary particles contained in the measurement sample obtained in the above preparation step is conducted.

In the obtained measurement sample, urinary particles, particularly casts and erythrocytes are stained by the aforementioned fluorescent dye. Therefore, these particles can be detected by observing the shapes and the degrees of staining of the particles in the measurement sample under a fluorescence microscope.

In a preferred embodiment, prior to the detection step, a step of obtaining optical information by irradiating urinary particles contained in the measurement sample with light is further conducted. The optical information obtention step is desirably conducted by a flow cytometer. In the measurement by a flow cytometer, by irradiating stained urinary particles with light when the particles pass through a flow cell, the optical information can be obtained as signals emitted from the particles. As such optical information, scattered light information and fluorescence information are preferred.

The scattered light information is not particularly limited as far as it is the information of scattered light that can be measured on a conventional commercially available flow cytometer. The scattered light information may include, for example, intensity and waveform information of scattered light such as forward scattered light (e.g. light receiving angle of about 0 to 20 degrees) and side scattered light (light receiving angle of about 90 degrees). More specifically, the scattered light information includes an intensity of scattered light, a pulse width of scattered light, an integral value of scattered light and the like. It is known in the art that side scattered light reflects the internal information of cells such as nuclei and granules, and forward scattered light reflects the information of the size of cells. In the embodiment, it is preferred to use the information of forward scattered light.

The fluorescence information is not particularly limited as far as it is the information obtained by irradiating the stained urinary particles with excitation light having an appropriate wavelength and measuring the excited fluorescence. The fluorescence information may include, for example, an intensity and a waveform of fluorescence. More specifically, the fluorescence information includes an intensity of fluorescence, a pulse width of fluorescence, an integral value of fluorescence and the like. The fluorescence is emitted from nucleic acid or the like in the particles stained by the fluorescent dye contained in the first reagent. The receiving wavelength can be appropriately selected depending on the fluorescent dye contained in the first reagent.

In the present embodiment, the light source of the flow cytometer is not particularly limited, and a light source having a suitable wavelength for excitation of the fluorescent dye can be appropriately selected. For example, a red semiconductor laser, a blue semiconductor laser, an argon laser, a He—Ne laser, a mercury arc lamp or the like may be used. In particular, a semiconductor laser is suitable because it is very low in price compared with a gas laser.

In the method of the present embodiment, when the aforementioned obtention step is conducted, at least casts and erythrocytes are detected as urinary particles in the detection step, based on the optical information obtained in the obtion step. The term "detection" embraces not only finding the existence of the urinary particles in the measurement sample but also classifying and counting the urinary particles.

In the present embodiment, detection of the urinary particles is preferably conducted by preparing a scattergram having two axes of scattered light information and fluorescence information, and analyzing the obtained scattergram by using appropriate analysis software. For example, when a scattergram is prepared having a fluorescent intensity on the X-axis and a forward scattered light intensity on the Y-axis, respective groups (clusters) appear on the scattergram in accordance with the particle size and the stainability (nucleic acid content) of the respective urinary particles. In the method of the present embodiment, at least casts and erythrocytes can be detected as two groups appearing in different areas. An analysis software provides windows which enclose the respective groups on the scattergram and allows count the number of particles in each window.

[Reagent for Analysis of Urine Sample]

A reagent 11 for analysis of urine sample of the present embodiment (hereinafter, simply referred to as "reagent") is a reagent for detecting at least casts and erythrocytes as particles in a urine sample. The reagent of the present embodiment contains at least one fluorescent dye selected from DiOC2(3), DiOC3(3), DiOC4(3) and DiOC5(3). The details of the reagent of the present embodiment are the same as those described for the first reagent used in the method for analyzing urine sample of the present embodiment.

The scope of the present invention also encompasses use of a reagent containing at least one fluorescent dye selected from DiOC2(3), DiOC3(3), DiOC4(3) and DiOC5(3), for detecting at least casts and erythrocytes as particles in a urine sample. FIG. 1 shows one example of the reagent 11 of the present embodiment.

[Reagent Kit for Analysis of Urine Sample]

A reagent kit for analysis of urine sample of the present embodiment (hereinafter, simply referred to as "reagent kit") is a reagent kit for detecting at least casts and erythrocytes as particles in a urine sample. This reagent kit comprises a first reagent containing at least one fluorescent dye selected from DiOC2(3), DiOC3(3), DiOC4(3) and DiOC5(3), and a second reagent containing a surfactant as a dispersant.

The details of the first reagent and the second reagent included in the reagent kit are the same as those describe for the first reagent and the second reagent used in the method for analyzing urine sample of the present embodiment.

Figure 2:
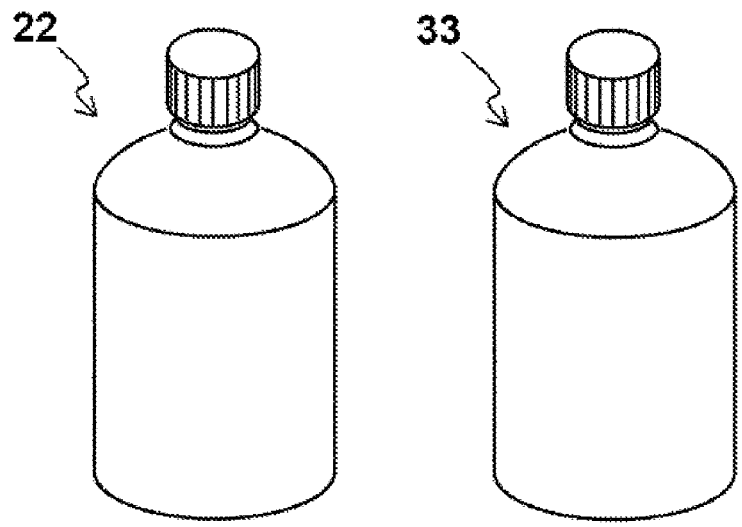
FIG. 2 shows one example of a reagent kit for analysis of urine sample.

In the present embodiment, it is preferable to store the first reagent and the second reagent in separate containers so as to provide a two-reagent type reagent kit comprising these reagents. FIG. 2 shows one example of a reagent kit of the present embodiment including a first reagent 22 stored in a container, and a second reagent 33 stored in a container.

The scope of the present invention also encompasses use of a reagent kit including a first reagent containing at least one fluorescent dye selected from DiOC2(3), DiOC3(3), DiOC4(3) and DiOC5(3), and a second reagent containing a surfactant as a dispersant, for detecting at least casts and erythrocytes as particles in a urine sample.

The present invention is further described in detail hereinafter by way of examples which do not limit the present invention.

EXAMPLES

Example 1

In Example 1, search for a dye capable of staining casts, and capable of discriminating casts from mucus threads according to the difference in staining was made. Discrimination between casts and mucus threads was conducted by observing a sample under a fluorescent microscopy. Also, measurement by a flow cytometer was conducted.

(1) Urine Sample

The urine sample used was a urine containing casts and mucus threads.

(2) Reagent

Staining Reagent

As a staining reagent, staining solutions 1 to 29 respectively containing dyes listed in Table 1 were prepared. Any of these staining solutions was prepared by dissolving a dye in ethylene glycol (NACALAI TESQUE, INC.) so that the dye concentration was 1 mg/mL.

TABLE 1

| Staining solution | Name of Dye | Basic structure | Source of supply |
|---|---|---|---|
| 1 | DioC2(3) | Cyanine | HAYASHIBARA CO., LTD. |
| 2 | DioC3(3) | Cyanine | HAYASHIBARA CO., LTD. |
| 3 | DioC4(3) | Cyanine | HAYASHIBARA CO., LTD. |
| 4 | DioC5(3) | Cyanine | HAYASHIBARA CO., LTD. |
| 5 | DioC6(3) | Cyanine | HAYASHIBARA CO., LTD. |
| 6 | DioC7(3) | Cyanine | HAYASHIBARA CO., LTD. |
| 7 | DioC18(3) | Cyanine | HAYASHIBARA CO., LTD. |
| 8 | SYTO | Cyanine | Life Technologies |
| 9 | YO-PRO | Cyanine | Life Technologies |
| 10 | NK-359 | Styryl | HAYASHIBARA CO., LTD. |
| 11 | NK-361 | Styryl | HAYASHIBARA CO., LTD. |
| 12 | FM4-64 | Styryl | Life Technologies |
| 13 | FITC | Xanthene | Life Technologies |
| 14 | Calcein | Xanthene | HAYASHIBARA CO., LTD. |
| 15 | Fluorescein Diacetate | Xanthene | HAYASHIBARA CO., LTD. |
| 16 | Fluorescein | Xanthene | HAYASHIBARA CO., LTD. |
| 17 | BCECF-AM | Xanthene | HAYASHIBARA CO., LTD. |
| 18 | Rhodamine 123 | Xanthene | HAYASHIBARA CO., LTD. |
| 19 | Acid Red 97 | Azo | HAYASHIBARA CO., LTD. |
| 20 | Acid Orange 8 | Azo | HAYASHIBARA CO., LTD. |
| 21 | Crocein Orange G | Azo | HAYASHIBARA CO., LTD. |
| 22 | NBD-Cl | Benzoxadiazole | HAYASHIBARA CO., LTD. |
| 23 | Astrazone Orange G | Methine | HAYASHIBARA CO., LTD. |
| 24 | Astrazone Orange R | Methine | HAYASHIBARA CO., LTD. |
| 25 | Rhoduline Orange | Acridine | HAYASHIBARA CO., LTD. |
| 26 | AY | Acridine | HAYASHIBARA CO., LTD. |
| 27 | Acriflavine Hydrochloride | Acridine | HAYASHIBARA CO., LTD. |
| 28 | 3,6-Diamino-10-methyl-acridinium Chloride | Acridine | HAYASHIBARA CO., LTD. |
| 29 | Euchrysine 2GNX | Acridine | HAYASHIBARA CO., LTD. |

Diluting Reagent

A diluting reagent used was HEPES-OH (100 mM, pH 7) (Dojindo Molecular Technologies, Inc.). As a solvent, water filtrated through a reverse osmosis membrane was used.

(3) Observation Under Fluorescence Microscope and Result

The urine sample (200 μL), the diluting reagent (580 μL) and each staining solution (20 μL) were mixed and allowed to react at 40° C. for 1 minute to prepare a measurement sample. Then casts and mucus threads in the obtained measurement sample were observed under a fluorescence microscope BX51 (Olympus Corporation). As a result of the observation, among the above 29 kinds of dyes, only six kinds of dyes, DioC2(3), DioC3(3), DioC4(3), DioC5(3), DioC6(3) and DioC7(3) were found as a dye capable of staining casts, and capable of discriminating casts from mucus threads according to the difference in staining. When these dyes were used, casts were stained favorably compared with mucus threads, and as a result, casts and mucus threads were discriminable from each other.

(4) Measurement by Flow Cytometer and Result

In association with the observation result under the fluorescence microscope, for the samples respectively stained with the staining solutions 1 to 6, whether casts and mucus threads are discriminable from each other was examined also by a flow cytometer. The samples were measured by using a flow cytometer UF-1000i (Sysmex Corporation). Specific steps of measurement by this flow cytometer are as follows. First, the urine sample (200 μL), the diluting reagent (580 μL) and each staining solution (20 μL) were mixed and allowed to react at 40° C. for 60 seconds to prepare the measurement samples. Then the measurement sample was irradiated with light, and the forward scattered light intensity, the side scattered light intensity, the fluorescence intensity and the integral value of fluorescence were obtained. The flow cytometer had a light source of a semiconductor laser having an excitation wavelength of 488 nm. From the fluorescence intensity and the integral value of fluorescence, a fluorescence intensity ratio and a cumulative fluorescence ratio of casts to mucus threads were calculated. The result is shown in Table 2.

TABLE 2

| Staining solution | Dye | Cumulative fluorescence ratio (casts/mucus threads) | Fluorescence intensity ratio (casts/mucus threads) |
|---|---|---|---|
| 1 | DioC2(3) | 3.4 | 4.3 |
| 2 | DioC3(3) | 3.2 | 4.9 |
| 3 | DioC4(3) | 5.3 | 5.9 |
| 4 | DioC5(3) | 3.5 | 4.4 |
| 5 | DioC6(3) | 1.2 | 1.2 |
| 6 | DioC7(3) | 1.3 | 1.3 |

As shown in Table 2, both of the fluorescence intensity ratio and the cumulative fluorescence ratio were greater than or equal to 1.2 in any case of using the staining solutions 1 to 6. In particular, it was revealed that the fluorescence intensity ratio and the cumulative fluorescence ratio were high when the staining solutions 1 to 4 were used. This result revealed that DioC2(3), DioC3(3), DioC4(3) and DioC5(3) are suited for discrimination between casts and mucus threads by a flow cytometer.

Example 2

In Example 2, influence on erythrocytes (hemolysis) by DioC2(3), DioC3(3), DioC4(3), DioC5(3), DioC6(3) and DioC7(3) was examined. Influence on erythrocytes was evaluated according to the number of erythrocytes in the measurement sample.

(1) Erythrocyte Sample

Human blood sampled from a healthy volunteer was diluted 1000 times in a saline (Otsuka Pharmaceutical Factory, Inc.) to prepare the erythrocyte samples.

(2) Reagent

As a staining reagent, the staining solutions 1 to 6 identical to those in Example 1 were used. As a diluting reagent, the buffer solution identical to that in Example 1 was used.

(3) Measurement and Result

The samples were measured by using a flow cytometer UF-1000i (Sysmex Corporation). The measurement sample was prepared in the same manner as in Example 1. Then the measurement sample was irradiated with light, and a fluorescence intensity and a forward scattered light intensity were acquired. The flow cytometer had a light source of a semiconductor laser having an excitation wavelength of 488 nm. Based on these measurement values, the number of erythrocytes in the measurement sample was counted. The result is shown in Table 3.

TABLE 3

| Staining solution | Dye | Total number of erythrocytes | Number of erythrocytes (cells/μL) |
|---|---|---|---|
| 1 | DioC2(3) | 16591 | 2127 |
| 2 | DioC3(3) | 15934 | 2043 |
| 3 | DioC4(3) | 16185 | 2075 |
| 4 | DioC5(3) | 14058 | 1802 |
| 5 | DioC6(3) | 44 | 6 |
| 6 | DioC7(3) | 39 | 5 |

As is apparent from Table 3, when the staining solutions 5 and 6 were used, the number of erythrocytes in the measurement sample significantly decreased in comparison with the cases where the staining solutions 1 to 4 were used. This reveals that erythrocytes are hemolyzed by the influence of DioC6(3) and DioC7(3) in the staining reagent. Therefore, in the cases where DioC6(3) and DioC7(3) are used in staining a urine sample, it is difficult to accurately count the number of erythrocytes in the sample. In contrast, it can be found that influence of DioC2(3), DioC3(3), DioC4(3) and DioC5(3) on erythrocytes is very small in comparison with those of DioC6(3) and DioC7(3), and thus are suited for measuring erythrocytes in a urine sample.

Example 3

In Example 3, the clinical performance of the method for analyzing urine sample using a flow cytometer according to the present embodiment was evaluated in comparison with the result of the visual observation.

(1) Urine Sample

The urine samples used were negative urine samples (42 samples) in which appearance of casts were not observed by observation under a microscope.

(2) Reagent

Staining Reagent

As the staining reagent, the staining solution 2 (containing DioC3(3)) identical to that in Example 1 was used.

Diluting Reagent

As diluting agents, diluents 1 and 2 having the following compositions were prepared. For the diluents 1 and 2, water filtrated through a reverse osmosis membrane was used as a solvent.

Diluent 1: HEPES-OH (100 mM, pH7) and EDTA-2K (25 mM) (Chubu Chelest Co., Ltd.)

Diluent 2: HEPES-OH (100 mM, pH7), EDTA-2K (25 mM) and DTAB (10 ppm) (TOKYO CHEMICAL INDUSTRY CO., LTD.)

(3) Measurement and Result

The samples were measured by using a flow cytometer UF-1000i (Sysmex Corporation). Specific steps of measurement by this flow cytometer are as follows. First, the sample (200 μL), the diluting reagent (580 μL) and the staining reagent (20 μL) were mixed and allowed to react at 40° C. for 10 seconds to prepare the measurement samples. Then the obtained measurement samples were irradiated with light, and the forward scattered light intensity, the side scattered light intensity and the fluorescence intensity were obtained. The flow cytometer had a light source of a semiconductor laser having an excitation wavelength of 488 nm. Based on these measurement values, the number of casts in the measurement samples was calculated, and the number of the samples that were decided as negative by the flow cytometer (FCM) was determined. Also the specificity of the analysis of casts by the FCM was determined by referring to the number of negative samples by the visual observation (microscopic observation). The result is shown in Table 4.

TABLE 4

| | Diluent 1 | Diluent 2 |
|---|---|---|
| Number of negative samples by visual observation | 42 | 42 |
| Number of negative samples by FCM | 30 | 36 |
| Specificity (%) | 71.4 | 85.7 |

Table 4 reveals that by treating a urine sample with the staining reagent containing DioC3(3) and the diluent, and measuring the obtained measurement sample by FCM, the urine sample can be analyzed with the specificity of greater than 70%. Also, by treating a urine sample with a diluent containing DTAB which is a cationic surfactant as a dispersant, the specificity was improved. This is attributable to the fact that impurities which resemble casts were reduced by the action of DTAB.

The present application relates to Japanese patent application No. 2014-39281 filed on Feb. 28, 2014, and the entirety of these claims, description, figures and abstract are incorporated into the present specification by reference.

REFERENCE SIGNS LIST

11: Reagent for analysis of urine sample
22: First reagent
33: Second reagent

What is claimed is:

1. A method for analyzing a urine sample, comprising the steps of:
    staining casts and erythrocytes in the urine sample with a fluorescent dye by mixing the urine sample with a first reagent containing the fluorescent dye, the fluorescent dye being at least one selected from the group consisting of 3,3'-diethyloxacarbocyanine iodide (DiOC2(3)), 3,3-dipropyloxacarbocyanine iodide (DiOC3(3)), 3,3'-dibutyloxacyanine iodide (DiOC4(3)) and 3,3-dipentyloxacarbocyanine iodide (DiOC5(3)),
    dispersing aggregates of impurities in the urine sample with dodecyltrimethylammonium bromide by mixing a mixture of the urine sample and the first reagent with a second reagent containing dodecyltrimethylammonium bromide and obtaining a measurement sample,
    obtaining scattered light information and fluorescence information by irradiating urinary particles contained in the measurement sample with light, and
    detecting at least the casts and the erythrocytes as the urinary particles in the measurement sample based on the obtained scattered light information and fluorescence information.

2. The method for analyzing the urine sample according to claim 1, wherein the second reagent further comprises a chelating agent.

3. The method for analyzing the urine sample according to claim 2, wherein the chelating agent is ethylenediaminetetraacetate (EDTA) salt.

4. The method for analyzing the urine sample according to claim 1, wherein the first reagent comprises a water-soluble organic solvent.

5. The method for analyzing the urine sample according to claim 1, wherein the method further comprises a step of flowing the measurement sample through a flow cell.

6. The method for analyzing the urine sample according to claim 1, wherein the scattered light information is scattered light intensity.

7. The method for analyzing the urine sample according to claim 1, wherein the fluorescence information is fluorescence intensity.

8. The method for analyzing the urine sample according to claim 1, wherein a concentration of the fluorescent dye in the measurement sample is more than or equal to 0.1 μg/mL and less than or equal to 200 μg/mL.

9. The method for analyzing the urine sample according to claim 1, wherein a concentration of the fluorescent dye in the measurement sample is more than or equal to 1 μg/mL and less than or equal to 20 μg/mL.

10. The method for analyzing the urine sample according to claim 1, wherein a pH of the second reagent is higher than or equal to 5 and lower than or equal to 9.

11. The method for analyzing the urine sample according to claim 1, wherein a pH of the second reagent is higher than or equal to 6.5 and lower than or equal to 8.6.

12. The method for analyzing the urine sample according to claim 1, wherein a pH of the second reagent is higher than or equal to 7.0 and lower than or equal to 7.8.

13. The method for analyzing the urine sample according to claim 2, wherein a concentration of the chelating agent in the measurement sample is more than or equal to 0.1 mM and less than or equal to 500 mM.

14. The method for analyzing the urine sample according to claim 2, wherein a concentration of the chelating agent in the measurement sample is more than or equal to 1 mM and less than or equal to 100 mM.

* * * * *